United States Patent
Holt et al.

[11] 4,033,178
[45] July 5, 1977

[54] FLUID COUPLED TEST PROBE

[75] Inventors: Amos E. Holt, Lynchburg; Ronald N. Roseveare, Evington, both of Va.

[73] Assignee: The Babcock & Wilcox Company, New York, N.Y.

[22] Filed: Apr. 23, 1976

[21] Appl. No.: 680,014

[52] U.S. Cl. .......................................... 73/71.5 US
[51] Int. Cl.² .................................. G01N 29/00
[58] Field of Search ............... 73/71.5 US, 71.5 R, 73/67.8 R; 310/8.7

[56] References Cited
UNITED STATES PATENTS

| 3,255,626 | 1/1966 | Van der Veer | 73/71.5 US |
| 3,485,088 | 12/1969 | O'Connor | 73/71.5 US |
| 3,555,891 | 1/1971 | Lewis | 73/71.5 US |
| 3,741,003 | 6/1973 | Gunkel | 73/71.5 US |

Primary Examiner—James J. Gill
Assistant Examiner—Anthony V. Ciarlante
Attorney, Agent, or Firm—Joseph M. Maguire; John F. Luhrs

[57] ABSTRACT

A mobile fluid coupled test probe wherein communication between a transducer and an object under inspection is maintained through a fluid couplant which also serves to maintain engagement of the probe with the object.

8 Claims, 3 Drawing Figures

FLUID COUPLED TEST PROBE

This invention relates to a test probe and more particularly to a mobile test probe for the nondestructive testing of a workpiece wherein a piezoelectric transducer is fluid coupled to the surface of the workpiece for transmitting into and/or receiving from the workpiece ultrasonic acoustic waves.

An object of the invention is to provide a mobile test probe wherein a fluid couplant, such as water, serves as the medium for communication between a transducer, such as a piezoelectric transducer, and the surface of a workpiece.

A further object of the invention is to provide such a probe wherein the fluid couplant maintains engagement of the probe with the surface of the workpiece.

Still another object of the invention is to provide such a probe particularly adaptable to the inspection of curved or undulating surfaces.

Another object of the invention is to provide such a probe suitable for use in hostile environments, such as found in welding shops and the like.

A further object of the invention is to provide such a probe which is readily adapted for the propagation into and/or the receiving out of a workpiece longitudinal or shear waves.

Still another object of the invention is to provide such a probe wherein wastage of the fluid couplant onto the surface of the workpiece is minimized or maintained at a controlled rate.

These and further objects will be apparent from the following description taken in connection with the drawings in which:

IN THE DRAWINGS

DETAILED DESCRIPTION

Figure 1:
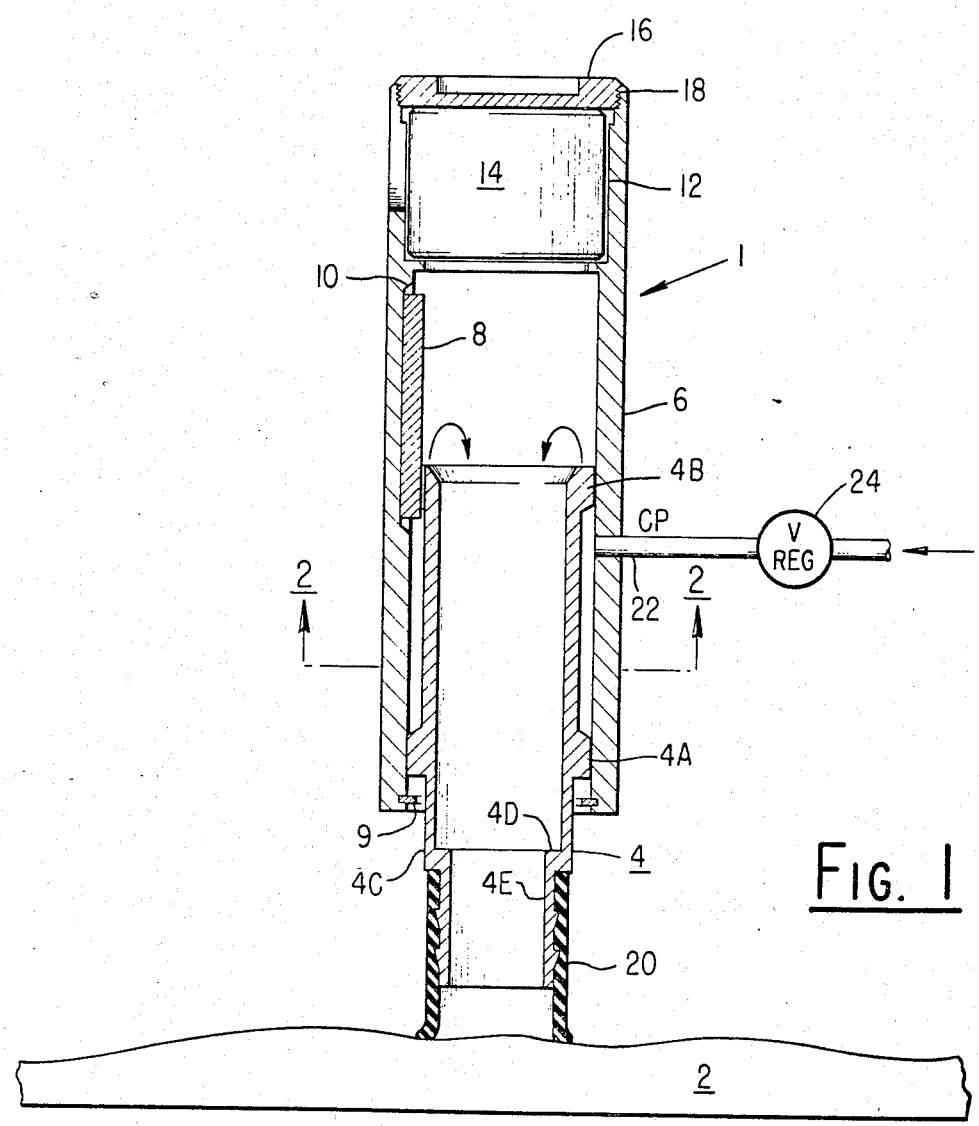
FIG. 1 is a sectional view of an embodiment of the invention.

Referring now to the drawings wherein like reference characters designate like or corresponding parts throughout the several views there is shown a test probe generally indicated at 1 arranged for the ultrasonic acoustic testing of a workpiece 2 having an undulating surface across which the probe may be move by manual or automatic means (not shown). The undulating surface of the workpiece as shown should be taken as representative of a wide variety of surfaces, such as, but not limited to, flat, round or spherical, the probe may scan.

Figure 2:
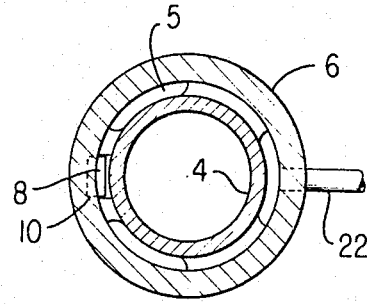
FIG. 2 is a sectional view taken along the line 2 — 2 of FIG. 1 in the direction of the arrows.

The probe 1 comprises a hollow compound piston, generally indicated at 4, reciprocatable within a cylinder 6, having axially spaced apart heads 4A and 4B, engaging the wall of the cylinder 6 and a cylindrical section 4C having an internal shoulder 4D and in the operating range extending beyond the open end of cylinder 6. As shown in FIG. 2, formed in the head 4B are a plurality of fluid passageways 5. If required, the piston 4 may be prevented from turning in the cylinder 6 by means of a key 8, secured to the wall of the cylinder 6, extending into a keyway 10 formed in the head 4B; or from being ejected from the cylinder 6 by means of a locking ring 9 carried in a groove formed in the cylinder 6. The end of the cylinder 6, remote from the workpiece 2, is formed to provide a receptacle 12 for receiving a transducer, such as a piezoelectric transducer 14. A closure 16 is axially adjustable by means of threads 18 as required to maintain the transducer 14 in proper position. The section 4C of piston 4 is provided with a nipple 4E for receiving, in fluid tight engagement, a flexible, pliable slide shoe 20 made, for example, of rubber, plastic or the like, having a memory, adapted to engage and self adjust to the surface of the workpiece 2, regardless of the contour thereof.

A flow of fluid couplant under pressure, such as water, from any suitable source (not shown), is introduced into the annular space between the piston 4 and cylinder 6 through a port 22, preferably located between the heads 4A and 4B and flows upwardly through the fluid passageways 5 and thence downwardly through piston 4 and flexible slide shoe 20, seeping onto the surface of the workpiece 2 in a minimal or controlled amount. Thus a solid column of fluid couplant is maintained between the surface of workpiece 2 and transducer 14 for the efficient transmission of ultrasonic acoustic waves therebetween.

The pressure of the fluid couplant acting on the upper annular surface of head 4A and shoulder 4D produces a force urging the slide shoe 20 into engagement with the surface of workpiece 2 in addition to that produced by the weight of the piston 4 when in other than a horizontal position. The pressure within the probe may be maintained to produce a controlled force of any desired value by means of an adjustable constant pressure outlet valve 24. Further, as the piston 4 in effect floats within the cylinder 6 as the probe 4 scans the surface of the workpiece 2, the force urging the shoe 20 against the surface will remain constant, regardless of the contour thereof, thus minimizing or, if desired, substantially eliminating, couplant seepage over the surface.

Usually the weight of the cylinder 6 produces a sufficient reaction force against the force produced by the couplant pressure. If required, additional weight may be added to produce the required reaction force. Conversely, if the reaction force produced by the weight of the cylinder 6 is too great, so that the piston 4 does not float between established limits within the range of operation of the probe, the effective weight of the cylinder can be reduced by providing a counteracting force such as might be produced manually or by a system or counterbalancing weights or springs. Similarly, when the probe is applied to a vertical or sharply inclined surface, the required reaction force can be obtained by manually pressing the probe toward the workpiece, or by a mechanical means such as a spring.

By introducing the fluid couplant into the annular space between the piston 4 and cylinder 6 and causing it to flow upwardly through the passageway fromed in the head 4B, a uniform flow distribution is assured. Further, by having the cylinder 6 of sufficient length so that with the piston 4 in a fully retracted position a space is maintained between the head 4B and receptacle 12, the elimination of eddy currents or the formation of a vortex is assured. However, if the exigencies of a particular application permit, the fluid couplant may be introduced between the head 4B and receptacle 12 and the space therebetween eliminated or substantially reduced.

Figure 3:
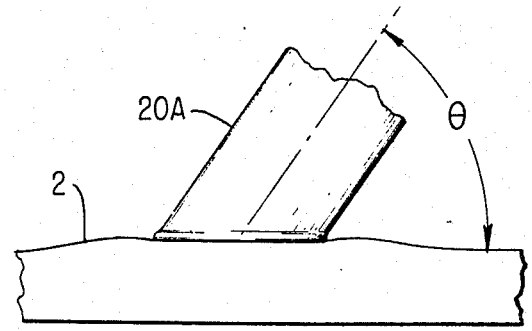
FIG. 3 illustrates a modification of the flexible shoe shown in FIG. 1 for engaging the surface of a workpiece when the probe is used for generating and/or receiving shear waves.

With the arrangement shown in FIG. 1, wherein the probe 1 is maintained substantially normal to the surface of the workpiece 2, longitudinal waves will be propagated into or received from the workpiece. In FIG. 3 there is shown a modification of the shoe 20, designated as a flexible slide shoe 20A, wherein the end of the shoe is formed so that when engaging the surface of the workpiece, the probe 1 will be at a desired acute angle, designated as the angle $\theta$ in the drawing, whereby shear waves are propagated into or received from the workpiece by the transducer 14.

While for purposes of illustration the probe 1 has been described specifically for the transmission and/or receiving of ultrasonic acoustic waves, it is apparent that the probe may be adapted to a wide variety of applications wherein a fluid couplant, either a gas or a liquid, is used to provide signal communications between a transducer and an object under inspection.

We claim:

1. A fluid coupled test probe for the nondestructive testing of materials, comprising in combination, a cylinder having a closed end and an open end, a receptacle formed in said cylinder adjacent said closed end for receiving a transducer, a hollow piston having a head slidably engaging the wall of said cylinder and extending beyond the open end of said cylinder for engagement of the end thereof with the surface of a workpiece, and means for introducing a flow of couplant fluid under pressure into said cylinder between said closed end and said piston head through said hollow piston onto the surface of the workpiece to thereby obtain a solid column of couplant fluid between the transducer and the surface of the workpiece and to produce a force on said piston head positioning said piston in said cylinder forcing to maintain said piston end into engagement with the surface of the workpiece as said probe is moved relative to the workpiece.

2. The combination as set forth in claim 1 wherein the end of said piston engaging the surface of the workpiece is flexible whereby peripheral engagement is maintained regardless of undulations in the surface of the workpiece.

3. The combination as set forth in claim 2 wherein the flexible end of said piston engaging the surface of the workpiece lies in a plane at right angles to the longitudinal center line of the probe.

4. The combination as set forth in claim 2 wherein the flexible end of said piston engaging the surface of the workpiece lies in a plane forming an acute angle with the center line of the probe.

5. The combination as set forth in claim 2 wherein said flexible end comprises a shoe of flexible, deformable material having a memory which thereby alters its shape to conform to the contour of the surface of the workpiece as the probe is moved relative thereto.

6. The combination as set forth in claim 1 further including means for maintaining a predetermined constant pressure of the couplant fluid within said cylinder to thereby cause said piston to reciprocate within said cylinder as required to maintain a constant engagement force with the surface of the workpiece as said probe is moved to scan the surface.

7. The combination as set forth in claim 1 wherein said piston is a compound piston having axially spaced apart heads, the head adjacent said closed end provided with a plurality of fluid passageways and said fluid couplant is introduced into said cylinder between said axially spaced apart heads.

8. The combination as set forth in claim 7 wherein said transducer is a piezoelectric transducer and said fluid couplant is water for the transmission of ultrasonic acoustic waves from said workpiece to said transducer and vice versa.

* * * * *